(12) United States Patent  
Holbeche

(10) Patent No.: US 8,828,326 B2  
(45) Date of Patent: Sep. 9, 2014

(54) DEVICE FOR GENERATING GASEOUS SPECIES

(75) Inventor: Thomas Bickford Holbeche, Church Crookham (GB)

(73) Assignee: Linde Aktiengesellschaft, Munich (DE)

( * ) Notice: Subject to any disclaimer, the term of this patent is extended or adjusted under 35 U.S.C. 154(b) by 308 days.

(21) Appl. No.: 13/510,030

(22) PCT Filed: Nov. 11, 2010

(86) PCT No.: PCT/GB2010/002069  
§ 371 (c)(1),  
(2), (4) Date: Jul. 18, 2012

(87) PCT Pub. No.: WO2011/061474  
PCT Pub. Date: May 26, 2011

(65) Prior Publication Data  
US 2012/0282574 A1    Nov. 8, 2012

(30) Foreign Application Priority Data

Nov. 17, 2009 (GB) .................................. 0920124.5

(51) Int. Cl.  
*B01J 19/08* (2006.01)  
*A61C 17/16* (2006.01)

(52) U.S. Cl.  
USPC .................. 422/186.04; 433/84; 433/216

(58) Field of Classification Search  
USPC ................................ 422/186.04; 433/216, 84  
See application file for complete search history.

(56) References Cited

U.S. PATENT DOCUMENTS

2006/0200122 A1* 9/2006 Sartor et al. ................. 606/41  
2011/0183284 A1* 7/2011 Yamanaka et al. .......... 433/32

FOREIGN PATENT DOCUMENTS

WO    WO 2007/067924    *  6/2007

* cited by examiner

*Primary Examiner* — Kishor Mayekar  
(74) *Attorney, Agent, or Firm* — David A. Hey

(57) ABSTRACT

The present invention provides a device 10 for generating a non-thermal gaseous plasma which may be a flow of gas plasma in the form of a gas plasma plume emitted from the device. The device comprises a gas capsule, or pressure vessel, 12 for holding a gas or gases 14 under pressure and forming a flow of gas through a plasma generator 16 to an applicator 18 when released from the capsule. Gas released from the gas capsule is energised in the reaction generator to form a gas plasma.

The device has a housing 28 for the plasma generator 16, a battery 116 and a signal generator 58 for energising the plasma generator. The gas capsule 12 docks with the housing 28. The device is adapted to be hand-held, typically by the gas capsule 12, and operated to allow it to be used for instance for cleaning and whitening teeth.

11 Claims, 7 Drawing Sheets

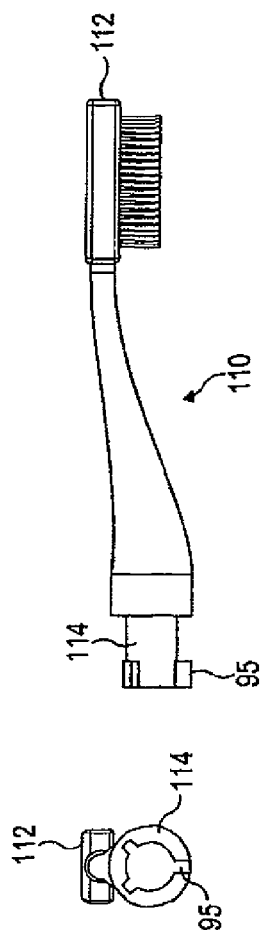
FIG. 6
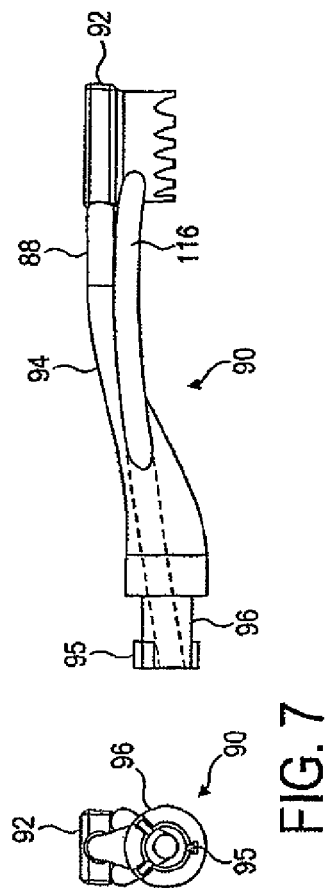
FIG. 7
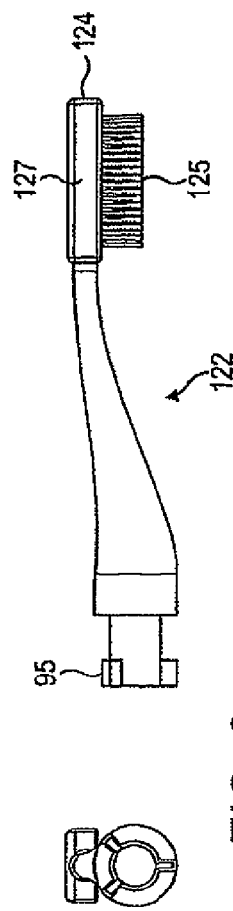
FIG. 8
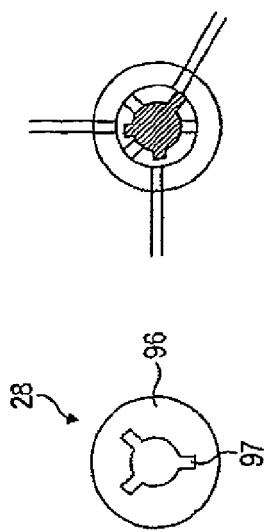
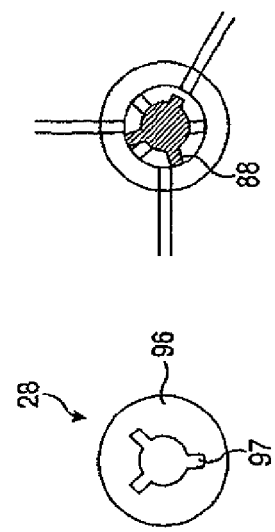
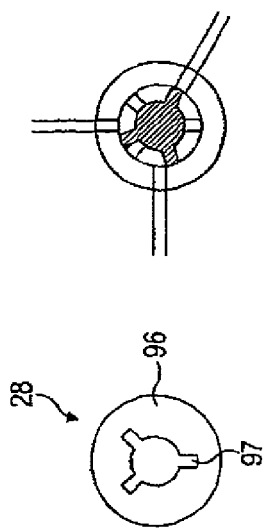

DEVICE FOR GENERATING GASEOUS SPECIES

FIELD OF THE INVENTION

The present invention relates to a device for generating gaseous species such as a non-thermal gas plasma and to an apparatus comprising the device.

BACKGROUND OF INVENTION

Systems for generation of non-thermal gas plasma are known hereto and have utility in a number of fields such as industrial, dental, medical, cosmetic and veterinary fields for the treatment of the human or animal body. Non-thermal gas plasma generation can be employed to promote coagulation of blood, cleaning, sterilisation, and removing of contaminants from a surface, disinfection, re-connection of tissue, and treatment of tissue disorders without causing significant thermal tissue damage. Examples of such systems are given in U.S. 2009/0009090 A1, WO 2009/065046 A1, and U.S. 2006/0084158 A1.

Known gas plasma generators are generally either industrial systems of considerable size for processing or functionalizing relatively large substrates or smaller systems comprising a base unit having a heavy duty gas cylinder connected by a gas line to a hand-piece. Additionally, the system may comprise a power unit connected by a power cable to the hand piece. These systems are not therefore well suited to domestic or in-surgery use.

SUMMARY OF THE INVENTION

The present invention provides a device for generating a flow of a non-thermal gaseous plasma, comprising: a gas caspule for releasably holding a gas under pressure; a plasma generator in which gas released from the capsule can be energised to generate said flow of non-thermal gaseous plasma; an applicator of the non-thermal gaseous plasma for directing the non-thermal gaseous plasma or an active gas derived therefrom at a surface to be treated; a source of electrical energy; energising means electrically connected to the source of electrical energy for energising gas in the reaction generator to form said non-thermal gaseous plasma; and a housing for housing the plasma generator, source of electrical energy, and energising means, the housing having an external port to which the gas capsule can be docked and a passage therethrough which when open can conduct gas released from the capsule to the plasma generator, wherein when the capsule is in its closed position the device can be held and operated by a user by hand to direct the flow of the non-thermal gaseous plasma from the applicator at a surface to be treated thereby.

The non-thermal gaseous plasma may have a temperature less than 40° C.

A gaseous plasma contains ions and electrons. A gaseous plasma typically also contains excited atoms or molecules. These excited atoms or molecules are chemically active and can cause the formation of free radicals in ambient gas. The activated atoms or molecules may have a longer half life than the ions and electrons. Thus, although the plasma may partially or completely decay or collapse in the applicator, it will still retain useful active species. The term "active gas" used herein encompasses such a decayed or collapsed plasma.

A control may be provided for selectively releasing gas from the gas capsule for forming said flow of gas. Said control may additionally be operably connected to said energising means for controlling energisation of the electrodes. A sensor may be provided for sensing the flow of gas released from the gas capsule and wherein said control allows activation of the energising means only if said flow of gas is above a predetermined mass or volume flow rate. The control may comprise a user input means, such as a manually operable button or switch, operable by a user for causing flow of gas to said reaction generator and activation of the energising means.

A gas release mechanism may be operable for releasing gas from the gas capsule when said gas capsule is docked with said housing. The gas capsule may comprise a pressure release valve, such as a Schrader valve, biased to prevent the release of gas from the gas capsule and said gas release mechanism comprises means for operating on said pressure release valve against said bias for releasing gas from the gas capsule.

The said passage may be provided with a flow valve which when open allows said flow of gas through the passage from the gas capsule to the plasma generator, and when closed resists said flow. Alternatively or additionally, a flow regulator may be provided for regulating the flow of gas between the gas capsule and the plasma generator and/or the flow of species from the plasma generator to the applicator. In this way, the flow of gas entering the entering the reaction chamber can be controlled to allow reaction to occur and the flow of species ejected from the device can be controlled to allow treatment to occur.

An expansion chamber may be provided in which gas can be released from the gas capsule for controlled release through an orifice plate. The expansion chamber reduces flow speed from the gas capsule.

The gas capsule contains a sufficient amount of gas prior to use for generating a species to treat a treatment region of an object or human or animal body for a time sufficient to achieve a beneficial effect on the treatment region. In this regard, the gas capsule typically contains a sufficient amount of gas for generating a plasma for at least two minutes. The generation of species sufficient to provide a beneficial effect on a treatment region (such as the teeth in an oral cavity) may require at least half a litre of gas per minute at atmospheric pressure. Accordingly, the gas capsule may contain the equivalent of up to four litres of gas at atmospheric pressure stored at a pressure of at least 60 bar. The internal volume of the gas capsule may be in the range of 50 ml to 200 ml. The gas capsule may be generally cylindrical and less than approximately 200 mm in length and less than 50 mm in diameter. In one example, the gas capsule has an internal diameter of 35 mm and a length of 135 mm.

The energising means may comprise at least one electrode for generating an electric field in said reaction generator and a signal generator for generating an electrical signal for driving said at least one electrode. If the species generated is a gas plasma, the energising means may be configured to generate a non-thermal plasma at a temperature which is preferably less than about 40° C. which is tolerable by a user. At least one of said electrodes may be insulated from gas in the plasma generator by a dielectric to reduce arcing and thereby limit heating of the species. Said at least two electrodes may be spaced apart one from another in order to generate an electric field in substantially all of said plasma generator. One of said electrodes may be formed around a periphery of the plasma generator. One of the electrodes may be formed by a probe extending into the plasma generator. The probe may be tapered at an end portion thereof to form a point for increasing the generation of plasma in said plasma generator.

Said signal generator may be configured to generate pulsed DC or AC signal for driving said electrodes, which signal may be so modulated as to form a low duty cycle signal in which the energy is provided to the or each of the electrodes for less than 20% of the cycle. Indeed the generation of the gas plasma may be initiated in the plasma generator and continue without requiring continuous energisation by the energising means.

Said energising means may comprise an amplifier for amplifying the signal for driving the electrodes and a matching circuit for matching impedance of the load and the source.

The source of electrical energy may be one or more batteries. The batteries are preferably rechargeable and said housing comprises a socket for receiving a plug connected to a mains power source and a recharging circuit for recharging the batteries. Alternatively, the device may comprise means for inductively coupling the batteries to a recharging unit for recharging. The housing may comprise an enclosure for locating the batteries in the housing and electrical terminals which connect to the batteries when located in said enclosure for supplying energy to said energising means.

Alternatively, the source of electrical energy may comprise a transformer and said housing comprises means for connecting the transformer to an electrical power supply and wherein said transformer is adapted to supply energy to said energising means.

The applicator may comprise a port in the housing communicating with the plasma generator. The applicator may comprise an applicator head for applying species and a duct for ducting species from said reaction chamber to said head. The applicator head may be spaced from said plasma generator thereby separating the treatment region from the energising means, which may typically be high voltage.

The device has many applications but may be adapted to treat an oral region of a human or animal body by whitening or cleaning teeth. In this regard, the applicator head may be sized and shaped to fit over one or more teeth. The applicator head may comprise one or more channels configured to be located in the mouth of a human or animal body for directing species for treating a plurality of teeth.

Evacuation means may be provided for evacuating species from the treatment region after treatment and may comprise pumping means driven by a motor for pumping species from the treatment region. An exhaust duct may extend from the treatment region and be in fluid communication with said pumping means. The exhaust duct may be formed by said applicator. The control may additionally control operation of said evacuation means together with the supply of gas to the reaction chamber and activation of the energising means. The evacuation means causes a flow of gas or species from the treatment region which is preferably greater than said flow of gas to the treatment region caused by release from said gas capsule.

A display may be provided for displaying a value representative of a condition of said device which be one or more of: the gas content of the capsule, the amount of charge remaining in the source of electrical energy, or a temperature of the plasma emitted from the device. Means may be provided for alerting a user, such as a sound which is audible to user or a warning light, when a condition of said device decreases below a predetermined amount.

The gas capsule may contain a gas having low energy requirement for forming a plasma in said reaction chamber. In this way, the amount of energy injected into the reaction chamber can be reduced thereby avoiding excessive heating of the gas or species. The gas may be a noble gas such as helium. A non-thermal plasma of a noble gas comprises a mixture of ions and electrons. The half life of the plasma may be so short that it collapses before it exits the applicator. The plasma also contains excited atoms. It is believed that some noble gas atoms remain in an excited state after collapse of the plasma. Excited noble gas atoms react with atmospheric gases including water vapour to form free radicals such as oxygen atoms and hydroxyl radicals. Such free radicals are believed to have beneficial bactericidal properties. Accordingly, it is not essential that any collapse of the non-thermal gaseous plasma follows its discharge from the applicator.

In order to permit the device to be used by hand, it is preferable that when assembled with the capsule docked with the housing, the device is less than 300 mm in length and 50 mm in breadth and has a mass of less than 1 kg.

BRIEF DESCRIPTION OF THE DRAWINGS

In order that the present invention may be well understood, embodiments thereof, which are given by way of example only, will now be described with reference to the accompanying drawings, in which:

FIG. 6 shows a first applicator of the device and a connecting portion of the device housing;

FIG. 7 shows a second applicator of the device and the connecting portion of the device housing;

FIG. 8 shows a third applicator of the device and the connecting portion of the device housing;

The drawings, particularly FIGS. 1 and 2, are not to scale.

DETAILED DESCRIPTION OF ILLUSTRATED EMBODIMENTS

Figure 1:
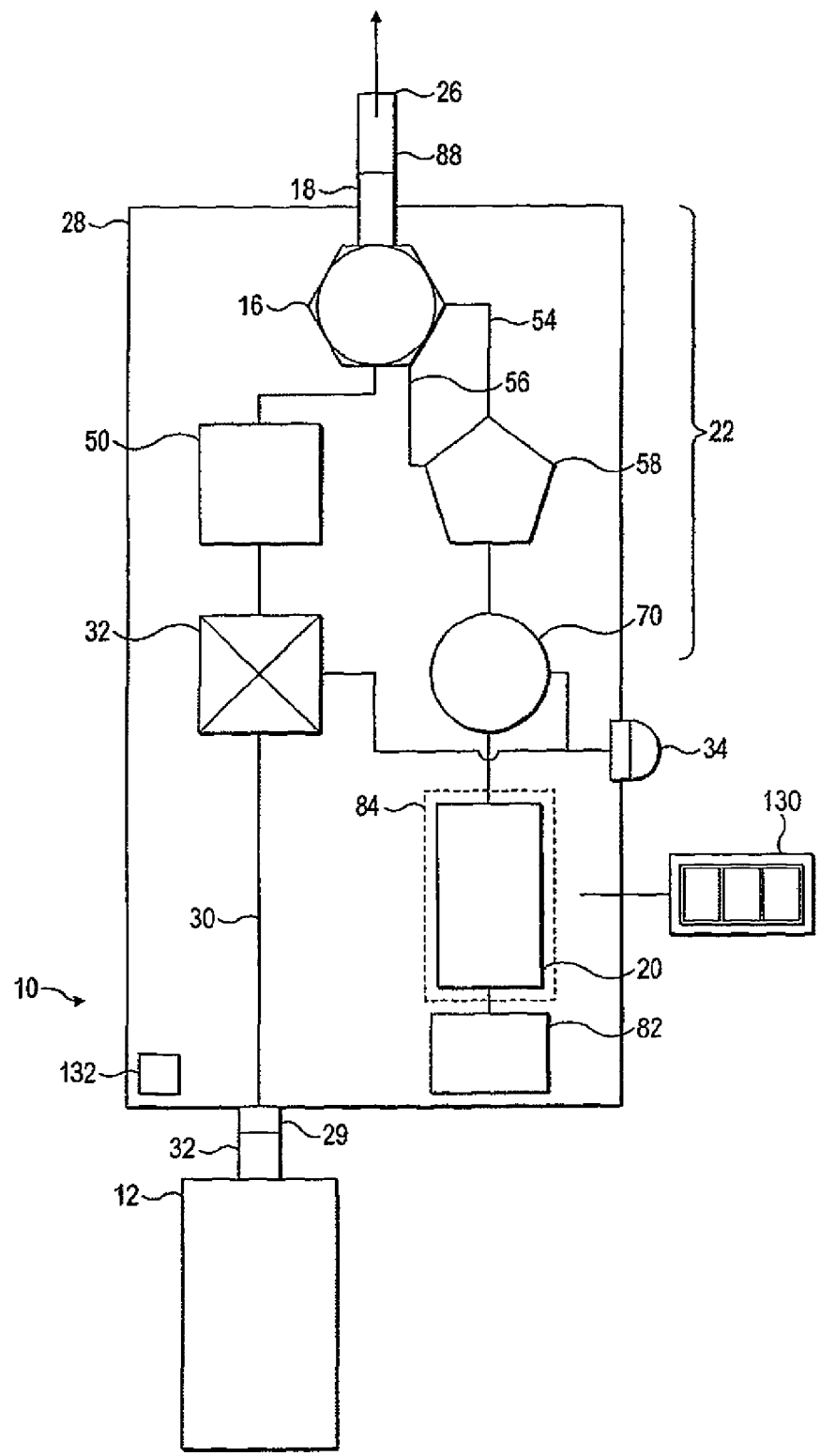
FIG. 1 shows schematically apparatus comprising a device for generating a non-thermal plasma.

Referring to FIG. 1, a device 10 is shown for generating a non-thermal plasma 24 which may be a flow of gas plasma in the form of a gas plasma plume emitted from the device. The flow of gas plasma is generated and emitted from the device generally at atmospheric pressure. The device comprises a gas capsule, or pressure vessel, 12 for holding a gas under pressure and forming a flow of gas through a plasma generator 16 to an applicator 18 when released from the capsule. Gas released from the gas capsule is energised in the plasma generator to form a non-thermal gas plasma. The gas may be a single pure gas or a mixture of two or more gases.

The device further comprises a source of electrical energy 20 and gas plasma energising means 22 electrically connected to the source of electrical energy for energising gas 14 in the plasma generator 16 to form a non-thermal gas plasma. The applicator 18 directs flow of plasma from the plasma generator 16 for generating a gas plasma plume from an opening 26 in the applicator. Gas plasma may be mixed with ambient air in a suitably configured applicator or may mix with ambient air on its discharge from the applicator.

A housing 28 houses plasma generator 16, source of electrical energy 20, and plasma energising means 22. The housing has an external port 29 with which the gas capsule 12 can be docked. The device is sized and of a weight such it can be held, the gas capsule 12 typically functioning as a handle, and operated by a user by hand and the plasma 24 readily directed by a user to treat a treatment region of an object or human or animal body. In this regard, the device is operable without the requirement for its connection by a gas line to a remote gas supply. Such a prior art arrangement is cumbersome and does not allow the device to be readily portable. When the gas capsule 12 is docked with the housing 28 the self-contained arrangement of the device 10 allows easy use in a domestic environment, for instance, in a bathroom. The device 10 may receive power from the source without the requirement for electrical cabling connecting the device to a mains supply. However, typically electrical cabling is less of an impediment to use in the domestic environment than a gas line, as cabling is usually flexible and light-weight, although in device 10 electrical cabling is not required when the device is in use.

In order that the device is suitable to be held and operated by hand, it should not exceed an upper size or an upper weight. It will also be appreciated that treatment of a treatment region using the device may require intricate and fine movements which are possible if the device is hand-held only if it is relatively light. In one example, the device is approximately the size and mass of a typical electric tooth brush. Other known hand-held and operated devices in other fields, which are provided herein to aid understanding of the size and mass of the device 10, are for example an electric tooth brush, or cordless electric drill or screw driver. The upper limit of the breadth is determined by the ability of a hand to hold the device. Any size of gas capsule significantly above 60 mm diameter renders the device uncomfortable to hold and use. The upper of the length is determined by the ability of a user to use the device without it becoming unwieldly and it will also be appreciated that if the device is used to treat teeth, the length of the device is desirably less than an arm's length and preferably in the region of about 20 cm to 25 cm. Preferably, the gas capsule 12 is contoured to so that it can be held comfortably in the palm of the hand. The mass of the device as a whole, is preferably less than one kilogram.

The device may be configured for use in a single treatment and then be disposable. In this regard, the components of the device are selected for only a single treatment. As a single treatment may require less gas and less energy stored in the device, the pressure vessel and source of energy can be selected to minimize manufacturing costs and reduce the size and weight of the device. For example, the device may be configured to treat an oral cavity only once and then be disposable. Such a disposable device may be more easily portable for instance in a jacket pocket or hand-bag. As the device is suitable for dry cleaning teeth or other treatment, a disposable device can readily be used whilst travelling for example since water is not always available for performing a treatment.

The device 10 may be used for example in the dental, medical, cosmetic and veterinary fields for the treatment of the human or animal body. The device has particular utility in dental or other oral treatments, for example, teeth whitening or cleaning of teeth, treatment of gingivitis, periodontis or halitosis, sterilization after root canal treatment, wound sterilization or healing (for example dry pockets after extractions), interdental cleaning and breath freshening. The application for teeth whitening is described in more detail in the applicant's co-pending application number GB 0823435.3 filed 23 Dec. 2008, the contents of which are hereby incorporated by reference. In this regard, the treatment region may be a single tooth, two teeth or the upper and/or lower arch of teeth. Alternatively, the treatment region may be a portion of the gingiva or a pocket. Still further, the treatment region may be the oral cavity.

The device 10 may also be used in applications such as the treatment of surfaces by plasma processing, for example, the preparation of a plastics surface prior to the application of a paint.

The components of device 10 will now be described in more detail, giving modifications and alternatives where relevant.

The device 10 is fitted with a valve 33 which when open allows the flow of gas through a passage 30 from the gas capsule 12 to the plasma generator 16, and when closed resists flow. The valve 33 may be mechanically linked to a mechanical push switch 34 which can be operated by a user for controlling the valve 33. Alternatively, other user activation means can be provided to operate the valve, such as a mechanical slide switch or an electronic switch which can be closed for example to open a solenoid valve. Still further, the user activation means may be adapted such that flow can be activated from the gas capsule in response to first user input and deactivated in response to a second user input. Alternatively, a single user input may activate a timer circuit (not shown) to allow gas flow for a predetermined period of time sufficient to treat a treatment region. For example if the device 10 is used for teeth whitening the predetermined period may be 5 seconds for each tooth.

The valve 33 may be any suitable means for opening and closing flow between the gas capsule and the plasma generator. Further, the valve 33 may be variable for adjusting the flow between fully open and fully closed.

As stated above, the housing 28 comprises a port 29 in which the gas capsule 12 can be docked so that the gas capsule is operable to release gas for forming the gas flow. The gas capsule 12 may be provided with its own valve 32. The gas capsule may be formed with a head which receives the valve 32 and which has an external surface that makes a sliding fractional fit or a bayonet coupling with the port 29 or which has a screw-threaded external surface which engages complementary screw threads in a member on the housing 28 that defines the port 29. Whatever kind of engagement the gas capsule makes with the port 29, it is such that the gas capsule 12 can be removed from the housing 28, for example, when the gas contained therein is depleted so that a replacement gas capsule which is full can be docked with the housing.

The housing may comprise a formation or other gas release mechanism operable for releasing gas from the gas capsule when the gas capsule is docked with the housing. The valve 32 may have a valve member biased to prevent the release of gas from the pressure vessel. The gas release mechanism operates on the pressure release valve against the bias for releasing gas from the capsule.

Figure 4:
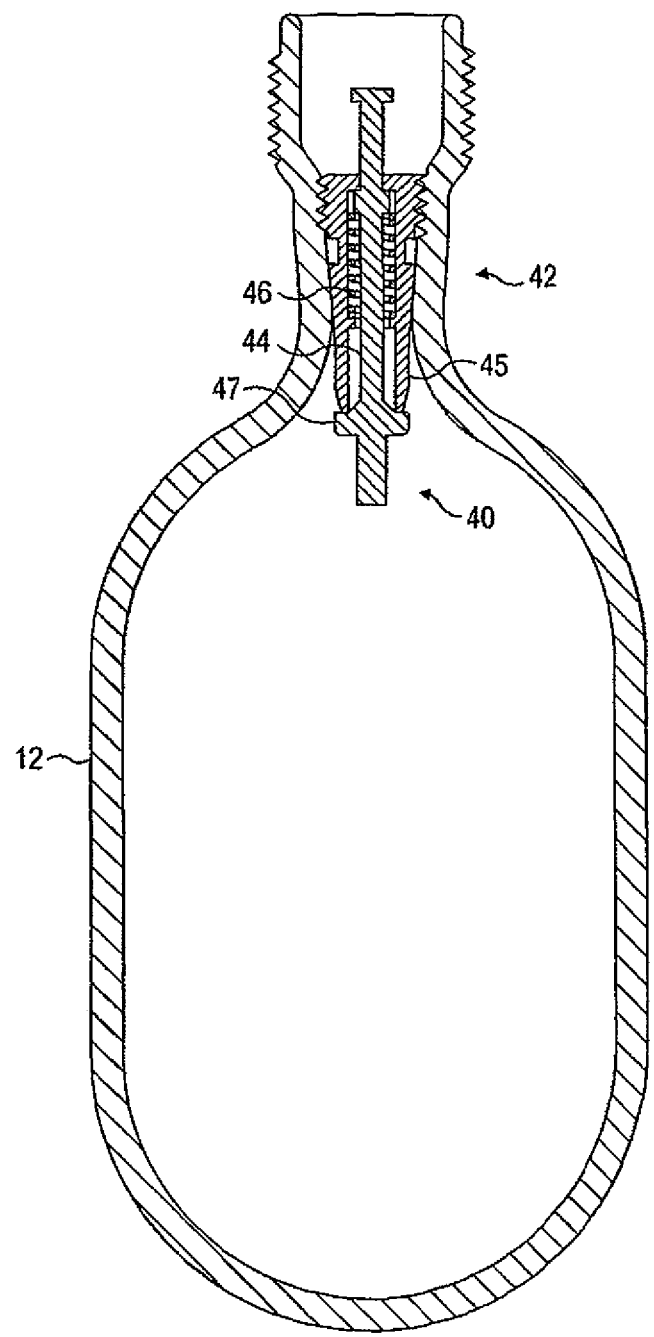
FIG. 4 shows a cut-away view of a pressure vessel of the device.

One example of the gas capsule 12 showing a suitable form of valve 32 is shown in FIG. 4. The gas capsule 12 comprises a valve 32 at the head 42 of the capsule. In this example locating means comprises an outer surface of the head 42 which is threaded for engaging with a complementary threaded surface of the housing for locating the pressure vessel in position. The valve 32 comprises a sliding member 44 received for sliding movement in the neck of the pressure vessel and biased by a biasing means, which in this example is a spring 46, into a closed position. The sliding member 44 extends through a sleeve 45 which has external screw threads engaging fluid-tight complementary screw threads formed in the inner surface of the head 42. The inner end of the sleeve 45 forms a valve seat. When the pressure vessel 12 is docked with the housing 28 the sliding member 44 is urged into the vessel moving a valve member 47, integral with the sliding member 44, away from the seat and opening the valve to allow gas flow from the vessel. The valve 32 has sufficient sealing strength to retain gas in the pressure vessel at the maximum pressure of the vessel, for example, 80 bar. The valve may be a Schrader valve.

Figure 3:
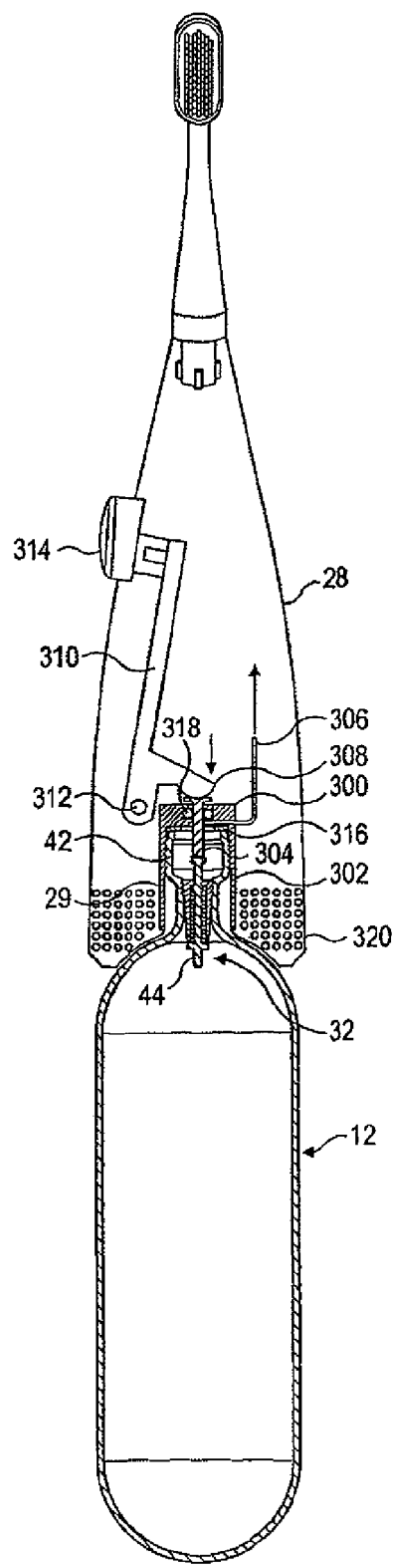
FIG. 3 shows a schematic side view of the device illustrating the docking of the capsule with the housing.

One arrangement for opening the valve 32 is shown in FIG. 3. For ease of illustration, parts not essential for an understanding of the mechanism for opening the valve 32 are not shown in FIG. 3. The housing 28 has a docking port 29 with internal screw-threads that are complementary to external screw-threads on the head 42 of the capsule 12. Docking of the capsule 12 with the housing 28 is thus a simple operation. The docking port 29 is provided by a disc 300 having an integral skirt 302. A push rod 304 extends through an axial bore in the disc 300. The disc 300 is formed with an internal passage communicating with a conduit 306 leading to the non-thermal plasma generator (not shown in FIG. 3). When the capsule 12 is first clocked with the housing 28 the bearing ends of the push rod 304 and the sliding member 44 are in close proximity. The top (as shown) of the push rod 304 cooperates with a cam 308. The cam 308 is connected to or integral with an actuating rod 310 which has a pivot 312. The activating rod 310 is operable by means of a push button 314 provided at the exterior of the housing 28 to cause the cam 308 to move about the pivot 312 and urge the push rod 304 against the sliding member 44, displacing it in a valve-opening direction. The valve 32 is thus opened and gas is thereby caused to flow from the capsule 12 through the disc 300 to the conduit 306 and thence to the plasma generator (not shown in FIG. 3). In order to prevent leakage of gas, a first O-ring sealing member 316 is provided between the head 42 of the capsule 12 and the disc 300 and a second O-ring sealing member 318 is provided between the push rod 304 and the axial bore through the disc 300. If desired, the docking port 29 may also be configured so as to enable a battery charger (not shown) to be inserted to enable the battery of the device to be recharged. The port 29 may thus be surrounded by an inductive charging coil 320 within the housing 28.

Referring again to FIG. 1, the mass or volume flow rate of gas entering the plasma chamber 16 is preferably controlled to promote the generation of non-thermal gaseous plasma. For instance, the rate of flow controls the residence time of gas in the plasma chamber. If the rate is too high, the resulting gas plasma may contain an undesirably low concentration of excited atoms, ions and electrons. Additionally, the flow through the applicator may be more than is required to achieve a beneficial result of the treatment region and therefore wasteful of gas. If the rate of flow is too slow, insufficient plasma flow may be generated through the applicator resulting in inadequate treatment of the treatment region or generation of an undesirable or non-therapeutic gaseous species. Accordingly, the device 10 comprises a flow regulator 50 for regulating the flow of gas between the gas capsule and the plasma generator. Additionally or alternatively, a flow regulator can be located to regulate the flow of gas and plasma from the plasma generator. The flow regulator may be a variable flow control valve arranged in a feed back loop with a flow sensor (not shown in FIG. 1). As an alternative to a flow regulator, a pressure regulator may be provided for regulating the pressure of gas in the plasma generator. Preferably, the flow regulator is operable to achieve constant flow of gas to the plasma generator throughout a pressure range of gas in the gas capsule that is, relatively high pressure when the capsule is full and relatively low pressure when the capsule becomes empty.

Figure 2:
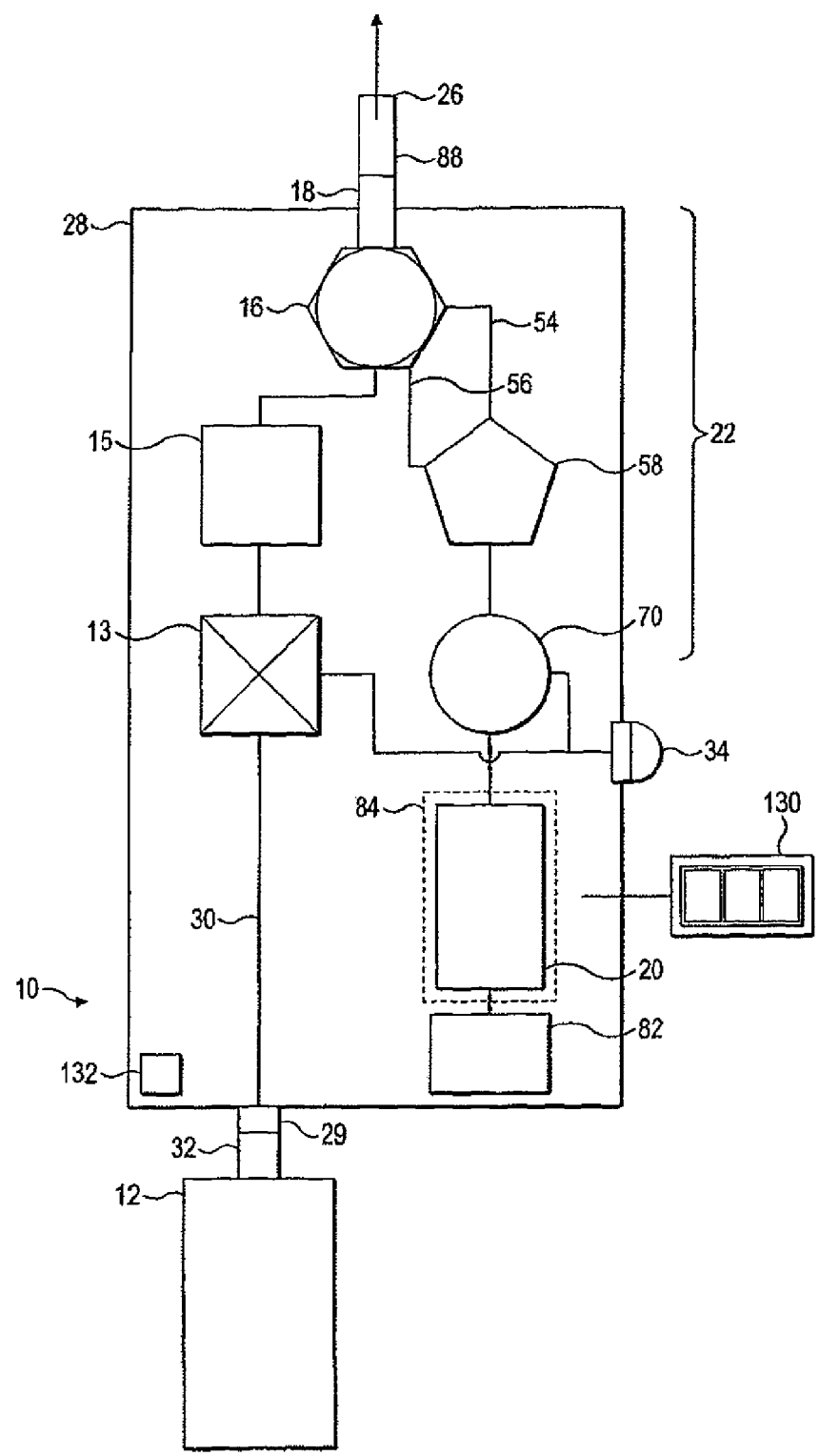
FIG. 2 shows a modified device or the kind shown in FIG. 1.

In an alternative form of the device shown in FIG. 2, the flow or pressure regulator 50 may be omitted and replaced by an orifice place 13 for controlling the flow rate of gas from the capsule 12 and an expansion chamber 15 for allowing the gas to expand to a lower pressure upstream of the plasma generator 16. In addition, the valve 33 is omitted.

The required amount of exposure of a treatment region to the non-thermal gaseous plasma (or other gas species generated by the plasma) varies depending on the type of treatment which the device 10 is adapted to perform. Accordingly, the gas capsule contains a sufficient amount of gas prior to use for generating a plasma to treat a treatment region of an object or human or animal body for a time which is sufficient to achieve a beneficial, or therapeutic, effect on the treatment region. For example, if it takes 5 seconds to whiten a single tooth at a flow rate of one litre per minute, and a typical mouth contains 32 teeth, the gas capsule should contain at least 2.66 litres of gas at atmospheric pressure. Preferably, the gas capsule contains sufficient gas and operates at lower flow rates for a plurality of treatments.

The gas capsule may contain a sufficient amount of gas for generating a plasma plume for at least two minutes or the generation of a plasma plume sufficient to provide a beneficial effect on a treatment region.

The amount of gas which can be contained in the pressure vessel, or gas capsule, is limited by the design of the pressure vessel and overall weight and size of the device. In this latter regard, a relatively heavy pressure vessel may be capable of storing large quantities of gas, however, such a heavy vessel is not suitable for the device 10 as it would render the device incapable of being held and operated by hand. It has been found that a suitable gas capsule is adapted to contain the equivalent of approximately four litres of gas at atmospheric pressure stored at a pressure of at least 80 bar and typically up to 200 bar. The gas capsule may have an internal volume sufficient to contain between 10 ml to 100 ml of water. The gas capsule may be generally cylindrical and less than 100 mm in length and 35 mm in diameter. In the example shown in FIG. 3, the gas capsule is approximately 135 mm in length and 35 mm in internal diameter. The vessel may be made from aluminium or stainless steel, or mild steel or any other suitable robust material, including fibre reinforced materials.

Referring again to FIG. 1, the plasma energising means 22 comprises two electrodes 54, 56 for generating an electric field in the plasma generator 16. In certain configurations a single electrode may be provided and more than two electrodes may be provided for example with two electrodes receiving a driving signal and one electrode being earthed. A signal generator 58 generates an electrical signal for driving, or energising, the electrodes. At least one, and preferably both or all, of the electrodes are dielectric barrier discharge electrodes insulated from gas in the plasma chamber by a dielectric to prevent excessive heating of the plasma caused by continuous or prolonged arcing. Suitable dielectric materials are ceramic, plastics or glass. Insulating the or each electrode reduces the duration of arcing in the plasma chamber when an electric current flows from one electrode through the plasma or gas to the other electrode or each of the other electrodes.

The electrodes 54, 56 are spaced apart one from another in order to generate an electric field in substantially all of the plasma chamber 16. In this way, it is possible to maximise the formation of plasma since gas in all portions of the plasma chamber interacts with the electric field.

One of the electrodes 54, 56 may be formed around a periphery of the plasma generator If the plasma generator is formed from a dielectric the electrode may be embedded in the structure of the wall of the plasma generator or on the outer surface of the wall. If the plasma generator is formed from an electrical conductor, the wall of the plasma generator itself may act as an electrode.

It has been found that plasma generation is promoted if one of the electrodes 54, 56 is formed by a probe extending into the plasma generator The probe is tapered at an end portion thereof to form a point for increasing the generation of plasma in said plasma generator. In this regard, the density of electric field is increased particularly in the region of the plasma generator proximate the point of the probe. The probe may be electrically insulated along its length with a dielectric.

The plasma energising means may 22 may operate in any of one or more plasma energising modes and can be capacitively coupled or inductively coupled to the plasma chamber. A timing circuit 62 may switch the signal output off and on over required duty cycle.

Alternatively, signal generator 58 is configured to generate a pulsed DC signal output at 4 kV and 8 kHz for driving the electrodes 54, 56. In another arrangement, signal generator 58 is configured to generate an AC signal output at 1 kV and 30 to 80 kHz for driving the electrodes 54, 56. This range is greater than 20 kHz so that signal generator is not typically audible to people during use. Use at less than 20 kHz may produce audible hissing.

An electrical switch 70 is provided which when closed allows energisation of the electrodes 54, 56. The switch 70 is manually operable by a user using the previously referenced button switch 34 (which also activates valve 33). Alternatively, a separate user input device may be used to operate switch 70. The use of the same user input device for controlling the flow of gas into the plasma chamber and the energisation of the electrodes 54, 56 is desirable because preferably gas flow and energisation of the electrodes occurs at the same time or there may be a predetermined time delay between gas flow and energisation. Further, it is preferable that energisation of the electrodes does not occur unless gas flow exceeds a predetermined minimum required flow.

Figure 5:
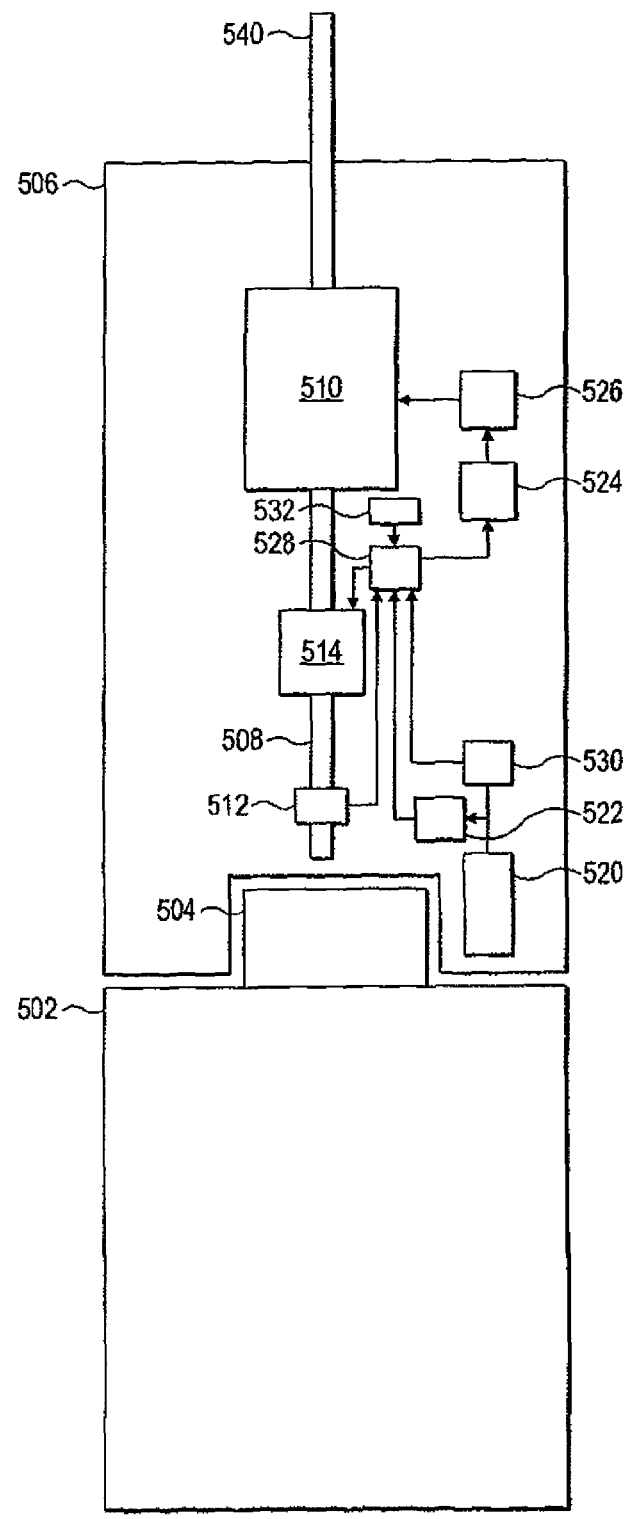
FIG. 5 shows schematically an arrangement for generating an AC plasma-generating signal from a battery.

Referring now to FIG. 5, there is shown schematically a form of the device according to the invention in which a 12V DC signal is converted to a 6 kV Ac signal for operating the plasma generator on a 15% duty cycle. A low duty cycle helps to preserve electrical energy in the device whilst not significantly affecting the formation of a plasma.

The device shown in FIG. 5 has a cylindrical gas capsule 502 of water capacity up to 100 ml. The gas capsule 502 is fitted with an on-off valve 504. The valve 504 may be of the same kind as described herein with reference to and as shown in FIG. 4. The valve 504 may be actuated by an arrangement similar to that described with reference to and as shown in FIG. 3. To prepare the device for operation, the gas capsule 502 is docked with a housing 506 which contains valves for controlling the supply of gas from the capsule to a generator of non-thermal gaseous plasma, the generator also being provided within the housing 506. In addition, the housing holds one or more electrical batteries for supplying a DC current, and electrical means for transforming the DC voltage to an AC voltage and for applying the AC voltage to the electrodes of the plasma generator.

The housing 56 has a gas passage 508 for flow of gas from the gas capsule 502 to a plasma generator 510. The passage 508 houses, in sequence, a pressure regulator 512, a flow sensor 514, and a solenoid valve 516, all upstream of the plasma generator 510.

The housing 506 holds a 12V battery 520. The battery is provided with a display LED 522. The display LED can indicate the status of the battery, i.e. it informs the user when the available power in the battery 520 is low. The battery 520 provides power to a low voltage signal generator 524 in combination with a high voltage generator 526. A control 528, in the form of a logic circuit, is configured to receive a plurality of inputs dependent on a condition of the apparatus for selectively supplying an output to the signal generators 524 and 526. A first input comes from a main on-off switch 530. If this switch is in its "off" position neither the gas supply nor the power supply to the plasma generator is able to be initiated. A second input may be from the LED 522. If the battery is low neither the gas supply nor the power supply to the plasma generator is able to be initiated. A third input to the control is from the flow sensor 514. If the flow sensor does not detect the flow of gas to the plasma generator 510, the power supply to the plasma generator 510 is not able to be initiated. Desirably, the logic circuit 528 includes time delay means which delays generation of a power output to the plasma generator 510 for a predetermined time after the flow sensor 514 senses the passage of gas to the plasma generator. This enables the gas to purge the plasma generator 510 prior to the initiation of plasma generation.

The device shown in FIG. 5 is provided with a secondary on-off switch 532. When the switch 532 is in its "off" position the solenoid valve 516 is in its closed position. Gas is therefore prevented from flowing to the plasma generator 510. On the other hand, when the switch is in its "on" position, the logic circuit sends a signal to the solenoid valve 516 so as to open it, provided the main switch 530 is also in its "on" position. The flow of gas to the plasma generator is therefore detected and a plasma generating signal is able to be sent to the plasma generator 510.

If desired, a single on-off switch may perform the functions of both the switches 530 and 532.

The plasma generator 510 has an outlet communicating with an applicator 540 configured to direct a plume of non-thermal gaseous plasma at a target surface.

The signal generators 524 and 526 may through a number of components and circuits (not individually shown) convert the electrical current from a 12V battery into a pulsed output voltage in the range 4 to 6 kV at a frequency of 2-10 kHz which is suitable for generation of a non-thermal plasma. Such circuits and components are well known in the fields of electronics and electrical engineering and need not be described in full detail herein. Essentially circuits of a kind used with xenon flashlamps can be used to enable the battery to charge a capacitor up to, say, 320V. A transformer can be used to set up the voltage and enable voltage pulses in the desired range of 4 to 6 kV to be generated. In order to produce clear, well defined pulses it is desirable to keep the number of turns and inductance of the windings of the transformer to low levels and to have modest step-up ratios. This approach helps keep the unwanted parasitic elements of leakage inductance and stray winding capacitance to a minimum, both of which contribute to pulse distortion.

Because a pulse transformer has a low primary winding inductance, the magnetising current that generates the working magnetic flux in the core is substantial, leading to significant stored magnetic energy in the transformer during the pulse generation. For an efficient design, this magnetic energy is recovered at the end of the pulse and temporarily held in another form (usually as a charge on a capacitor) ready to generate the next pulse.

In any case, the magnetic flux in the core is returned to zero before the next pulse is generated otherwise the flux builds up with successive pulses until the core saturates, at which point the transformer stops working and acts as a short circuit to the drive electronics.

A common method of magnetic energy recovery in switched-mode power supply transformers, which may be used in this case, is through the use of a so-called "flyback" winding. This is usually identical to the primary winding and both wound on the core at the same time (a bipolar winding) in order to ensure a high level of magnetic coupling between the two. The flyback winding connects between ground and the reservoir capacitor of the DC supply via a blocking diode.

During pulse generation a fixed voltage is applied to the primary winding and current ramps up building up magnetic flux in the core—this induces an equal and opposite voltage across the flyback winding (but no current flows due to the blocking diode). Interruption of the primary current at the end of the pulse forces the magnetic field to start collapsing which reverses the induced voltage across the flyback winding and causes current to flow back into the supply capacitor. The flux and current ramp down smoothly to zero ready for the next pulse.

Another suitable transformer configuration is a push-pull design in which two identical bifilar wound primary windings are alternatively connected to the DC power supply. The phasing of the windings is such that magnetic flux in the core is generated with opposing directions which each is alternately driven.

A push-pull design also allow stored magnetic energy to be recovered and returned to the supply capacitor in a very similar fashion to the flyback approach, where the blocking diode now becomes an active transistor switch. The same transformer design may now be used for either approach.

Although the push-pull design requires additional switching transistor and control, it allows the possibility of doubling the change in magnetic flux within the limits of the core by using both positive and negative flux excursions. The flyback design outlined above only allows unipolar flux excursions.

Referring again to FIG. 1, the source 20 of electrical energy may be one or more batteries and preferably the batteries are rechargeable. In this case, the housing 28 may comprise an electrical socket for receiving a plug connected to a mains power source and a recharging circuit 82 for recharging the batteries. Alternatively, the device comprises means for example primary windings in a recharging unit and secondary windings in the device connected to the batteries for inductively coupling the batteries to a recharging unit for recharging (as shown in FIG. 3).

The housing 28 comprises an enclosure 84 for locating the batteries in the housing and electrical terminals (not shown) which connect to the batteries when they are located in the enclosure for supplying energy to the plasma energising means 22.

In order to permit a free range of movement of the device by a user, it is preferable that the source of electrical energy is not connected to a mains or other supply during use. It will also be appreciated that as the device may be used in a wet environment for instance a bathroom it is advantageous to avoid cabling. Further, some bathrooms do not have an electrical socket. However, the device 10 may be connected by an electrical cable to a socket during use. In this case, the source 20 of electrical energy may comprise a transformer and the housing comprises a socket for receiving a plug connected to an electrical power supply. The transformer is adapted to supply energy in a form suitable for the plasma energising means 22.

Referring again to FIG. 1, the applicator 18 may take any suitable form for directing gas and plasma from the plasma generator 16 to a treatment region. In its simplest form the applicator may comprise an opening in the plasma chamber. However, as shown in FIG. 1, the applicator 18 comprises an opening 26 for forming the plasma plume and a duct 88 for ducting gas or non-thermal gaseous plasma from the plasma generator 18 to the head of the applicator. The duct 88 may be around 1 mm to 5 mm in diameter which is sufficiently small to cause a rapid through flow of plasma to the treatment region. The duct can be straight as shown or can be curvilinear to allow greater access to a treatment region. The applicator has a length which is typically less than about 10 cm. During its passage through the duct 88, the plasma tends to decay. It is believed, however, that in, for example, the case of a helium plasma, the excited helium atoms that are formed in addition to helium ions and electrons have a relatively long half life. These excited atoms will on encountering atmospheric gases, i.e. on leaving the applicator 18 react with them to form free radicals, such as hydroxyl radicals, that have a bactericidal action.

The head of the applicator may take the form of an opening or alternatively may comprise a nozzle for concentrating flow. The head is spaced from the plasma generator sufficient to protect a user from the high voltages used to generate the plasma and reduce the risk of contamination of the plasma chamber.

The applicator may also take the form of a conventional toothbrush head, but with orifices in the head for the discharge of non-thermal plasma communicating with a passage through the head.

In three examples as shown in FIGS. 6 to 8, the device 10 is adapted to treat an oral region of a human or animal body and the applicator head is configured to generate a plasma flow suitable for such oral treatment.

Referring first to FIG. 7, the applicator 90 comprises an applicator head 92, a central portion 94 having one or more ducts for ducting plasma to the head and also for ducting gas or plasma away from a treatment region, and a connecting portion 96 for connecting the applicator to the housing 28. Head 92 forms a cavity which is sized and shaped, and formed from flexible material to receive a treatment region for example two teeth. The cavity can alternatively be shaped to receive only one tooth or more than two teeth. The head 92 is adapted such that when the cavity receives the teeth substantially all of the surface area of the enamel of the teeth, and optionally a proximate portion of gingiva, is exposed to plasma or other active gas species for treatment.

The connecting portion 94 is configured to engage with a complimentary connecting portion 96 at an end of the housing 28 for fixing the applicator to the housing. The applicator connecting portion 94 comprises a plurality of formations, or keys, 95 which are received in a respective plurality of recesses, or key holes, 97 in the housing connecting portion 96. Once received in the recesses, the applicator and housing are relatively rotated to lock the applicator in place.

The connecting portions 94, 96 are configured to allow activation of one or more functions of the device 10 when connected and to prevent activation of functions when not connected. Similarly, the connection of one applicator to the housing may allow activation of one set of functions whilst the connection of another applicator to the housing may activate another set of functions. The connection of applicator 90 to housing 28 is configured to allow activation of the plasma energising means 22 and of gas flow to plasma chamber 16 when user input device 34 is operated. Without such connection, operation of the user input device cannot activate these functions.

Figure 9:
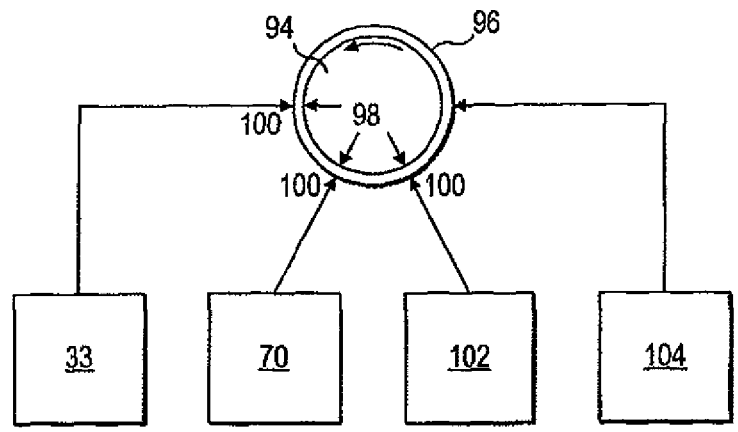
FIG. 9 shows schematically connection of the applicator shown in FIG. 7 to the housing.

As shown in FIG. 9, the connecting portions 94,96 may comprise complementary electrical contacts which are closed to allow activation of certain, selected, functions. In FIG. 9, the connecting portion 94 is rotatable in connecting portion 96 to lock the applicator to the housing. When locked, electrical contacts 98 on the connecting portion 94 contact electrical contacts 100 on the connecting portion 96 thereby closing respective electronic switches allowing activation of the gas flow by valve 33, activation of the plasma energising means by switch 70 and activation of evacuation means 102 (described below). Activation of means 104 for imparting motion to a tooth brush head is not allowed in this arrangement.

Figure 10:
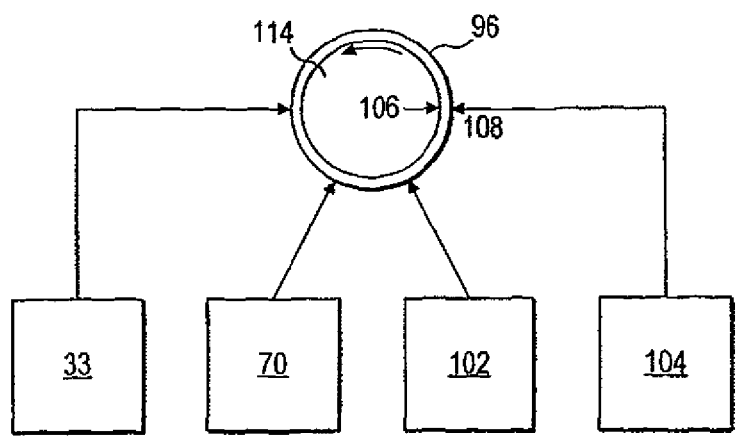
FIG. 10 shows schematically connection of the applicator shown in FIG. 8 to the housing.

When a different applicator is connected to the housing different functions of the device are allowed. In this regard, FIGS. 6 and 10 show schematically an applicator 110 illustrated. Applicator 110 comprises an applicator head 112 similar to a typical tooth brush comprising bristles for cleaning teeth. Applicator 110 further comprises connecting portion 114 for engaging with connecting portion 96 of the housing 28. Ducting is not required in applicator 110 between the connecting portion 114 and the head 112 as the applicator 110 is designed to be used without plasma treatment. As shown in FIG. 10, when connection portion 114 is received in connecting portion 96 and rotated to lock applicator 110 to the housing 28, electrical contact 106 on connecting portion 114 contacts electrical contact 108 on the connecting portion 96 thereby closing an electronic switch allowing activation of means 104 for imparting motion to a tooth brush head, or other means for aiding teeth brushing. The other functions of device 10 are deactivated in this arrangement so that plasma is not delivered when normal teeth brushing is performed.

Although applicator 110 is shown comprising an electrical contact for activating vibration for aiding teeth brushing, instead connecting portion 114 may be devoid of electrical contacts and the applicator 110 is then used as a normal tooth brush. If provided, vibration means 104 may comprise an electric motor for driving a drive shaft having an eccentric shaft portion connected to the applicator for vibrating, or otherwise moving, the applicator head 112. Alternatively, the motor is adapted to rotate the head to aid teeth cleaning.

Referring again to FIG. 7, applicator 90, comprises in central portion 94 a duct 88 for ducting plasma from the plasma chamber to the applicator head 92 and ducts 116 for ducting plasma or gas away from the treatment region. Ducts 116 form an exhaust duct in the applicator 90 extending from the treatment region and in fluid communication with evacuation means 102 shown in FIG. 9. The evacuation means comprises pumping means (not shown) which is driven by a motor (not shown) for pumping gas or plasma from the treatment region. The evacuation means 102 evacuates gas or plasma from the treatment region after treatment so that, particularly in oral treatment, a user does not inhale significant quantities of gas or plasma.

The exhaust gas exhausted by the evacuation means 102 may be used to cool the parts of the device susceptible to over-heating. The exhausted gas may be filtered by an activated filter.

Alternatively, a separate pumping means may be supplied to pump cool air over the internal components of the device. Still further of source of fluid such as carbon dioxide or water may be provided which can be released to cool the components. The internal components of the device 10 susceptible to heating may be provided with heat dissipation means such as fins or in a separate arrangement the device could be deigned to measure the electrical input and mass of gas input. Thus heat transfer could be measured and a safety feedback system designed.

A control is provided for controlling operation of the evacuation means. The control is preferably integrated with controls 30, 68 and comprises an electronic switch (not shown) for activating the motor operably connected to the user input device 34. Accordingly, the control is operable to control the evacuation means to evacuate gas or plasma from the treatment region when gas is supplied to the plasma chamber and the plasma energising means generates the plasma. In order to increase the efficiency of evacuation of plasma or gas from the treatment region, the evacuation means 102 is configured to cause a flow of gas or plasma away from the treatment region which is greater than the flow of gas caused by release from the gas capsule 12 and into the treatment region.

A third applicator 122 is shown in FIG. 8 which is generally similar to applicator 90 shown in FIG. 7 although with a different head and without the evacuation ducts 116. Applicator 122 comprises an applicator head 124 which comprises a plurality of fine hollow tubes 125 for directing plasma or active gas species onto a treatment region such as the teeth of a user. The fine hollow tubes may be formed by any suitable technique, such as extruding. The tubes are connected to a manifold cavity 127 in the head for distributing generally equally plasma or active species to the tubes.

Referring again to FIG. 1, the device 10 may comprise a display 130 for displaying a value representative of a condition of the device, for example, one or more of the gas content of the gas capsule 12, the amount of charge remaining in the source of electrical energy 20, or a temperature of the plasma plume emitted from the applicator. The display may be a graphical LCD. Additionally or alternatively, means 132 may be provided for alerting a user when a condition of the device, such as gas content of the pressure vessel, charge in the source of electrical energy, or temperature of the plasma plume decreases or increases beyond a predetermined amount. The alerting means 132 may comprise means for generating a sound which is audible to user or a warning light, such as an LED, prompting the user to recharge or replace the gas capsule or the source or to remove the device from the treatment region to avoid harm.

The gas capsule 12 preferably contains a noble gas or a mixture of noble gases, having low energy for forming a plasma in said plasma generator. That is, the gas can form a plasma when relatively low amounts of energy are input to the plasma generator 16 by the plasma energising means 22. In the formation of a gas plasma, the generated electric field causes high energy electrons to strike the gas atoms or molecules removing an electron thereby forming a sea of electrons and ions. Preferably the amount of energy required to achieve this effect is relatively low. The selection of a gas having such low energisation is advantageous because it facilitates the generation of a non-thermal plasma flow or plume at temperatures less than about 40° C. Relatively low temperatures are required when treating the human or animal body because high temperatures can kill biological cells causing necrosis or pain.

In use of the device 10 for example for whitening, cleaning, sterilising or healing an oral region of a body, a user selects an appropriate applicator 18 for fixing to the housing 28. Depending on the applicator, selected functions of the device 10 can be activated when the user operates the user input device 34. For plasma treatment, the operation of the user input device opens valve 32, closes switch 70 and activates the evacuation means 102. Provided there is sufficient gas flow (e.g. helium) into the plasma generator 16, the plasma energising means 22 energises gas in the plasma generator to form a plasma. Although substantially all of the plasma generator is exposed to an electric field, only a portion of the gas that enters the plasma generator may be energised to form a plasma. Accordingly, a mixture of gas and plasma flows from the generator and through the applicator 18. The user positions the applicator head so that the mixture of gas and plasma flows over the treatment region, for instance one or more teeth. During treatment, the evacuation means evacuates the mixture of gas and plasma from the treatment region. When treatment is completed, the user operates the user input device 34 to deactivate gas flow, the plasma energising means 22 and the evacuation means 102.

Inevitably, some plasma interacts with ambient air (e.g. oxygen, nitrogen and water vapour) causing some chemical break-down forming other active gaseous species, for example, hydroxyl radicals and free oxygen atoms, which have a bactericidal effect.

The invention claimed is:

1. A device for generating a flow of a non-thermal gaseous plasma, comprising:
   a gas capsule for releasably holding a gas under pressure;
   a plasma generator in which gas released from the capsule can be energised to generate said flow of a non-thermal gaseous plasma;
   an applicator of the non-thermal plasma for directing the non-thermal gaseous plasma or an active gas derived therefrom at a surface to be treated;
   a source of electrical energy;
   means electrically connected to the source of electrical energy for energizing gas in the reaction generator to form said non-thermal gaseous plasma; and
   a housing for housing the plasma generator, source of electrical energy, and energising means, the housing having an external port to which the gas capsule can be docked and a passage which when open can conduct gas released from the capsule to the plasma generator, wherein when the capsule is in its docked position the docked gas capsule acts as a handle for the device, and the device can be held and operated by a user by hand to direct the flow of the non-thermal gaseous plasma from the applicator at a surface to be treated thereby.

2. A device according to claim 1, comprising a control for selectively releasing gas from the gas capsule.

3. A device according to claim 2, wherein said control is operably connected to said energizing means for controlling activation thereof.

4. A device according to claim 3, comprising a sensor for sensing the flow of gas released from the gas capsule and wherein said control allows activation of said energizing means only if said flow of gas is above a predetermined mass or volume flow rate.

5. A device according to claim 1, comprising a pressure regulator for controlling flow of gas to the plasma generator.

6. A device according to claim 1, wherein the energizing means comprises at least one electrode for generating an electric field in said plasma generator and a signal generator for generating an electrical signal for driving said at least one electrode.

7. A device according to claim 6, wherein said signal generator is configured to generate a low duty cycle signal in which the energy is provided to the or each of the electrodes for less than 20% of the duty cycle.

8. A device according to claim 6 wherein at least one of said electrodes is insulated from gas in the reaction generator by a dielectric to reduce arcing.

9. A device according to claim 1, wherein said device is adapted to treat an oral region of a human or animal body by whitening or cleaning teeth.

10. A device according to claim 1, comprising means for evacuating gas or plasma from the treatment region after treatment.

11. A device according to claim 1, wherein the device is configured to generate non-thermal plasma at a temperature of less than 40° C.

* * * * *